(12) United States Patent
Nelson

(10) Patent No.: US 6,342,141 B1
(45) Date of Patent: Jan. 29, 2002

(54) SEALED EXHAUST SENSOR UTILIZING A MAT SUPPORT SYSTEM

(75) Inventor: Charles Scott Nelson, Clio, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/511,563

(22) Filed: Feb. 23, 2000

(51) Int. Cl.⁷ .............................. G01N 27/407
(52) U.S. Cl. .................. 204/426; 204/424; 204/428
(58) Field of Search ................ 204/421–429

(56) References Cited

U.S. PATENT DOCUMENTS 3,841,987 A * 10/1974 Friese et al.
3,960,692 A * 6/1976 Weyl et al.
4,088,555 A * 5/1978 Kita et al.
4,141,813 A * 2/1979 Kita et al.
4,157,282 A   6/1979 Riddel
4,198,279 A * 4/1980 Brown et al.
4,842,713 A * 6/1989 Stahl
4,986,892 A * 1/1991 Kato et al.
5,616,825 A   4/1997 Achey et al.

* cited by examiner

Primary Examiner—T. Tung
(74) Attorney, Agent, or Firm—Vincent A. Cichosz

(57) ABSTRACT

The present invention is an exhaust sensor seal and a method for making the same. A talc disk disposed between two support disks forms a talc assembly where at least one of which is metal. As pressure is applied to the assembly, the talc is forced into any voids in the sensing end of the exhaust sensor body from exhaust gases.

7 Claims, 3 Drawing Sheets

SEALED EXHAUST SENSOR UTILIZING A MAT SUPPORT SYSTEM

TECHNICAL FIELD

The present invention relates generally to exhaust sensors. More particularly, the present invention relates to a means for sealing a sensor in a mat supported exhaust sensor.

BACKGROUND OF THE INVENTION

Exhaust sensors are used in a variety of applications that require qualitative and quantitative analysis of gases. For example, exhaust sensors have been used for many years in automotive vehicles to sense the presence of oxygen in exhaust gases, i.e., to sense when an exhaust gas content switches from rich to lean or lean to rich. In automotive applications, the direct relationship between oxygen concentration in the exhaust gas and the air-to-fuel ratios of the fuel mixture supplied to the engine allows the exhaust sensor to provide oxygen concentration measurements for determination of optimum combustion conditions, maximization of fuel economy, and management of exhaust emissions.

A conventional stoichiometric exhaust sensor typically consists of an ionically conductive solid electrolyte material, a porous electrode on the sensor's exterior exposed to the exhaust gases with a porous protective overcoat, and a porous electrode on the sensor's interior surface exposed to a known oxygen partial pressure. Sensors typically used in automotive applications use a yttria stabilized zirconia-based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wall, according to the Nernst equation:

$$E = \left(\frac{RT}{4F}\right) \ln\left(\frac{P_{O_2}^{ref}}{P_{O_2}}\right)$$

where:

E=electromotive force

R=universal gas constant

F=Faraday constant

T=absolute temperature of the gas $p_{O2}^{ref}$=oxygen partial pressure of the reference gas $P_{O2}$=oxygen partial pressure of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric exhaust sensors indicate qualitatively whether the engine is operating fuel rich or fuel lean, without quantifying the actual air to fuel ratio of the exhaust mixture.

In conventional automotive exhaust applications, the body of an exhaust sensor utilizing talc for the dual purposes of sealing and sensor support has been prone to infiltration by exhaust fumes through undesirable internal air leaks in the exhaust sensor. Referring to FIG. 1, a prior art exhaust sensor has an upper ceramic disk 30 and a lower ceramic disk 32, between which is disposed a dual talc pack 34. The dual talc pack 34 supports the sensor element 6, and seals the exhaust sensor components from the exhaust gases. This configuration, however, has limited usefulness because the ceramic disks 32, 34 are generally about 5 millimeters thick or greater. This space requirement increases the overall required size of the exhaust gas sensor. Additionally, ceramic disks require the use of gaskets or other means for preventing stress points on the ceramic. Finally, since the dual talc pack 34 serves as the only means of supporting the sensor element 6, the talc seal is subject to breakdown due to mechanical disruption.

Sealing the internal components of an exhaust sensor from exhaust fumes would be useful, for example, in applications that require a clean air reference. What is needed in the art is a means for sealing the body of the exhaust sensor from exhaust fumes in a manner that conserves space while also assuring a durable seal.

SUMMARY OF THE INVENTION

The present invention is an exhaust sensor comprising: a shell; a talc assembly concentrically disposed within said shell, said talc assembly having a deformable talc disk; disposed between a first support disk and a second support disk, wherein at least one of said support disks is metal; and a sensor element disposed through said shell and said talc assembly; wherein said talc disk forms a seal against said shell and said sensor element.

The present invention also is a method for sealing an exhaust sensor comprising: positioning a talc assembly in a shell, said talc assembly comprising a talc disk disposed between support discs, wherein at least one of said support disks is metal; positioning an inner shield against the talc assembly; disposing a sensor element through said talc assembly; and applying force to the inner shield, thereby compressing the talc assembly and forming a seal between said talc assembly and said shell, and said talc assembly and said sensor element.

BRIEF DESCRIPTION OF THE DRAWINGS

Referring now to the drawings, which are meant to be exemplary and not limiting, and wherein like elements are numbered alike in the several Figures.

DESCRIPTION OF THE PREFERRED EMBODIMENT

The present invention relates to a unique means for sealing the body of an exhaust sensor from exhaust gases. The present invention comprises a sensor element disposed through a talc assembly, with at least a portion of the sensor element preferably surrounded by a mat support, and a talc disk disposed between support disks. When force is applied to the talc assembly, the talc compresses and fills any voids, thereby sealing the upper portion of the exhaust sensor body from exhaust gas.

Figure 1:
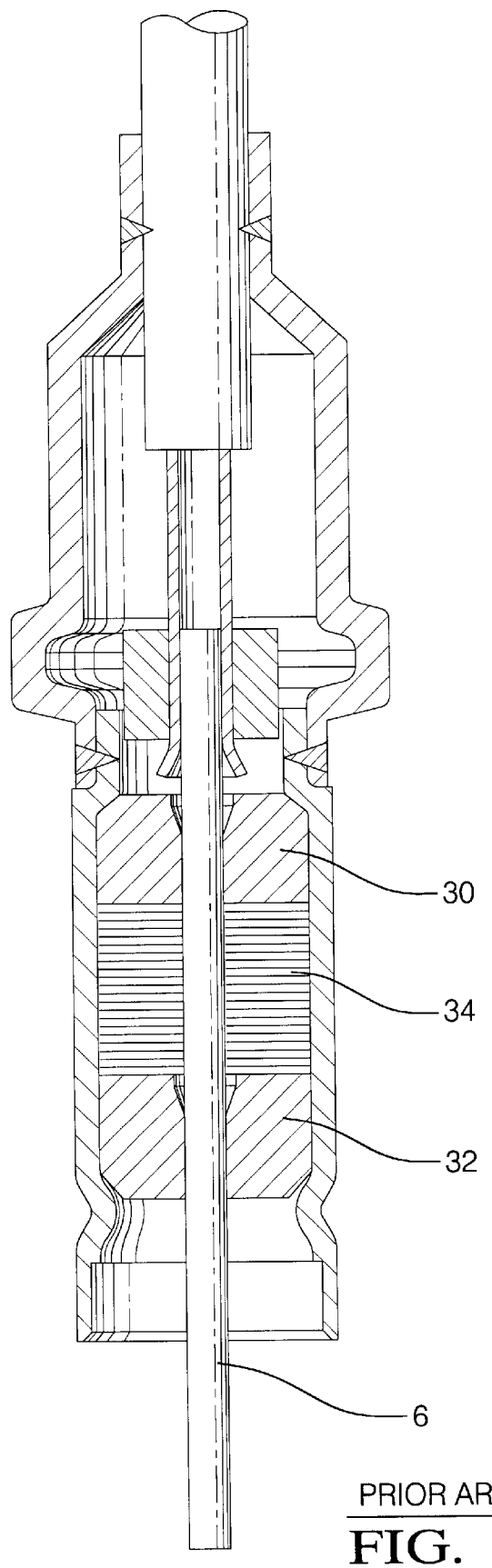
FIG. 1 is a cross-sectional view of a prior art exhaust sensor.
Figure 2:
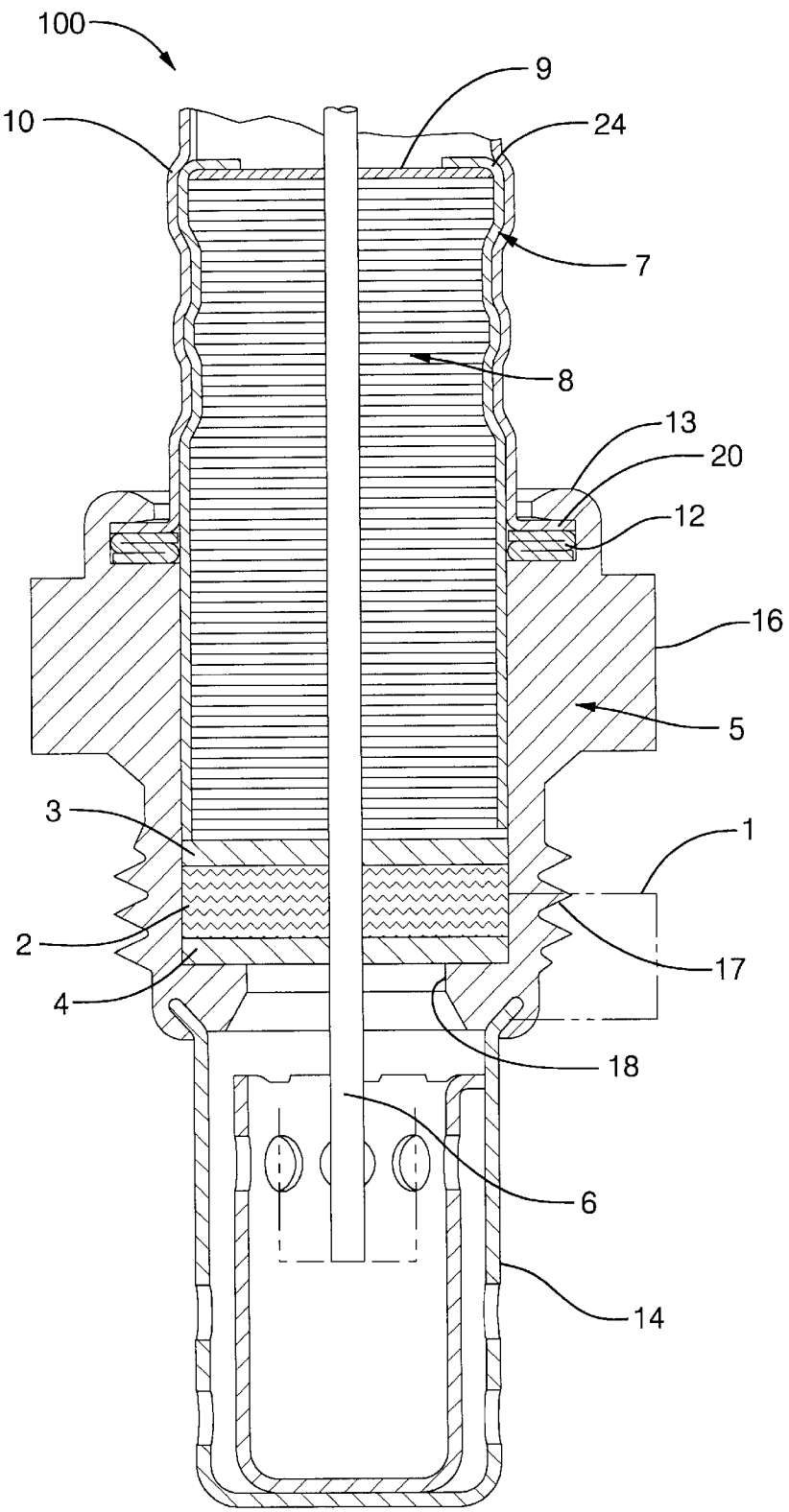
FIG. 2 is a cross-sectional view of one embodiment of a sealed exhaust sensor of the present invention.
Figure 3:
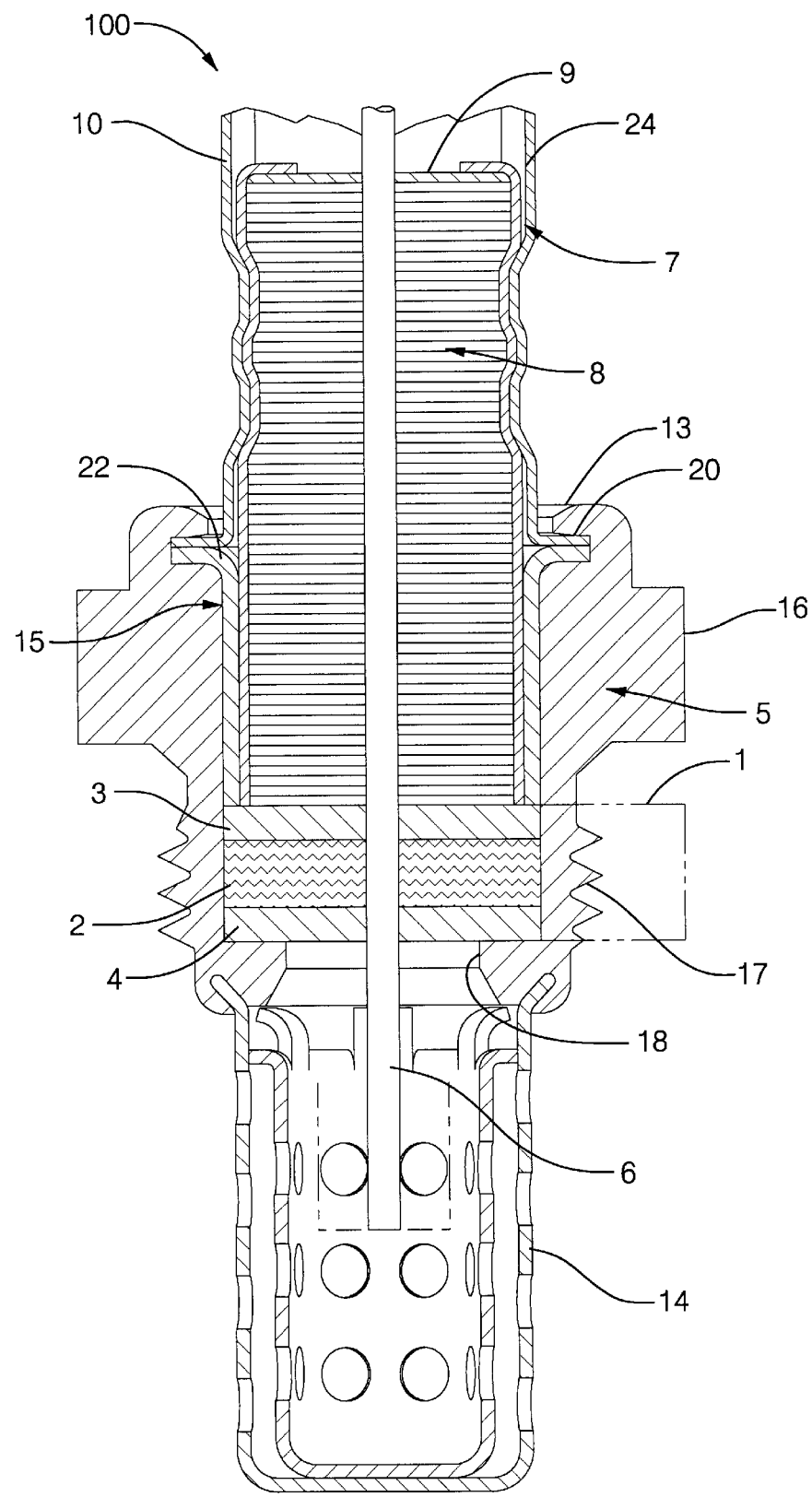
FIG. 3 is a cross-sectional view of a second embodiment of a sealed exhaust sensor of the present invention.

The exhaust sensor of the present invention is generally indicated as 100 in FIGS. 2 and 3, which illustrate two embodiments. The talc assembly 1 comprises a talc disk 2 disposed between an upper support disk 3 and a lower support disk 4. The talc disk 2 comprises talc having an average grain size from about 0.5 to about 10.0 micrometers, with an average grain size from about 6.0 to about 7.5 micrometers preferred. Additionally, the talc disk 2 should have sufficient thickness so that when pressure is applied thereto and the talc is therefore compacted, the talc will fill voids and form fluid tight seals. The talc disk 2 can be up to about 10 millimeters (mm) thick or greater, with about 1.5 to about 6 mm thick preferred. After compression, the talc disk 2 directly supports the sensor element 6.

The talc disk 2 is disposed in between the upper support disk 3 and the lower support disk 4. Both disks 3,4 position and restrain the talc disk 2 prior to the application of force on the talc assembly 1. Each disk 3, 4 has an aperture disposed approximately in the center of the disk 3, 4 into which the sensor element 6 may be inserted. The shape of the aperture is dependent upon the shape of the sensor element 6. For a planar sensor element 6, for example, the aperture preferably has a substantially rectangular geometry.

During assembly, the upper support disk 3 bears the compression force and preferably evenly distributes the force to the talc disk 2. The lower support disk 4 prevents excessive talc leakage into the lower shield 14 area. After initial compression of the talc assembly and final assembly of the exhaust sensor 100, the support disks 3,4 support the sensor element indirectly through the talc that has been forced into the space between the hole in each support disk 3,4 and the sensor element 6.

These support disks 3,4 can be made of a material compatible with the environmental conditions of the exhaust sensor 100, and capable of providing the desired structural support during assembly. It will be appreciated by those skilled in the art that after assembly, the support disks 3,4 maintain the disposition of the talc assembly, and thereby maintain the integrity of the talc seal. Specifically, the support disks 3,4 should be capable of maintaining structural integrity in a high temperature environment (up to about 1000° C.). Possible materials include metals, such as ferrous materials, with high chrome content stainless steels (above about 12%) preferred, and the like and alloys thereof.

The support disks 3,4 should be thick enough to be able to withstand force sufficient to compress the talc such that the talc flows into any voids and forms a fluid tight seal. Typically, a thickness sufficient to withstand a force which compresses the talc to a minimum of about 1,000 to about 3,000 p.s.i. along the edges can be employed. The disks should also be thin enough to flex under assembly pressure (see below). The thickness of the support disks is dependent upon the properties of the material used and whether it is the upper or lower support disk. For example, if the support disks 3,4 were made from SS 409 annealed, they would have a typical thickness of about 1.5 mm or less. Since the upper support disk receives and distributes the compressive forces to the talc while the lower support disk inhibits extrusion of the talc into the lower shield 14 area, it is preferable that the upper support disk 3 be more ductile than the lower support disk 4. Consequently, these disks can be composed of different materials and/or have different thicknesses.

As stated above, the support disks 3,4 and the talc disk 2 together form a talc assembly 1. The talc assembly 1 is disposed within a shell 5, and has a central aperture through which the sensor element 6 passes. An inner shield 7 can be disposed adjacent to both the shell 5 and the talc assembly 1. The inner shield 7 encloses a mat support 8, which is disposed between the sensor element 6 and the inner shield 7.

The shell 5 preferably includes a body portion 16 and a threaded portion 17. The body portion 16 is preferably shaped to accommodate a wrench or other tool for tightening the threaded portion 17 into a threaded hole in an exhaust pipe or other component of an exhaust flow system. Such tightening allows proper positioning of both the lower shield 14 and the terminus of the sensor element 6 within the flow of exhaust gas. The shell 5 holds the inner shield 7 in compressive force engagement, and further provides a shell shoulder 18 for contacting the talc assembly 1.

The optional mat support 8, which provides structural integrity to the sensor, comprises a mat material designed for use in a spark ignition engine environment, e.g., a mat material designed to withstand continuous exposure to temperatures from about 300° C. to about 1,000° C. Such materials include ceramics, metals, and composites, and mixtures and alloys thereof, in the form of fibers (bundled, woven, nonwoven, random, continuous, chopped, etc.), mesh, cloth, and other forms. The mat support 8 may be installed in either a preform or fibrous blanket type state around at least a portion of sensor element 6.

A restraint 9, which is typically a metal, ceramic or composite plate, can be disposed between the mat support 8 and an upper shoulder 24 of inner shield 7 in order to prevent movement of the mat. An upper shield 10, which is disposed around at least a portion of inner shield 7, encloses the upper elements (not shown), which include conventional components such as electrical connectors and a seal enclosing wires that provide an electrical link to the outside of the sensor. The upper shield 10 preferably has a connector that secures the upper shield 10 to the shell 5. For example, an outward flare 20 or a similar connector can be disposed on the terminus of the lower edge of shield 10, between a sealing gasket 12 and a shell crimp 13.

The shields 7, 10, 14 and shell 5, can be any material compatible with the operating environment and which provides the desired structural integrity. Possible materials include metals (such as steel and the like), composites, and alloys chosen for high temperature endurance, strength, and corrosion resistance, with a high chrome or high nickel stainless steel preferred.

Installation of the talc assembly 1 and sealing of the sensor can be accomplished by first inserting the talc assembly 1 into the shell 5 until the lower support disk 4 of the talc assembly 1 is flush with the inner surface of the shell shoulder 18. In one embodiment, which is represented in FIG. 2, the sensor element 6 and the inner shield 7 with mat support 8 and metal restraint 9 are then installed by applying a force to the inner shield 7 in the direction of the talc assembly 1. The shell crimp 13 is then crimped over the outward flare 20 and the crimp gasket 12 to hold the upper shield 10 in place.

Alternatively, the upper shield 10 can be assembled to inner shield 7 before insertion into shell 5. In this embodiment, the crimp gasket 12 is first installed, and then the combined inner shield 7 and upper shield 10 assembly is fitted into the shell 5. Force applied to the upper shield 10 is transferred through the inner shield 7 to the upper support disk 3. To complete assembly, the shell crimp 13 is crimped over the flared lower edge of the upper shield 10, and the lower shield 14 is crimped into place.

In another embodiment, shown in FIG. 3, a cylindrical push ring 15 is disposed between the inner shield 7 and the shell 5. This push ring 15 is disposed against the upper support disk 3, and has a bend 22, such as a substantially 90° bend, on its upper edge, which abuts outward flare 20 of the upper shield 10. In this embodiment, installation of the talc assembly 1 and sealing of the sensor is accomplished by first installing the talc assembly 1 in the shell 5. The sensor element 6, push ring 15, and the inner shield 7 with mat support 8 and metal restraint 9 are then installed, and a force is applied to the push ring 15 in the direction of the talc assembly 1. The upper shield 10 is then installed, and the shell crimp is crimped over the outward flare 20 of the upper shield 10 to secure the assembly.

In any of the above embodiments, the force applied to the top support disk 3 results in the forcing of talc from the talc disk 2 into any voids that exist in the areas surrounding the talc assembly 1, including the sensor element 6, the shell 5, the upper support disk 3, and the lower support disk 4. Alternatively, the force may be applied to the upper shield 10, which will transfer the force through the inner shield 7, to the top support disk 3, and finally to the talc disk 2. The crimp gasket 12 will take up any tolerance stackups. The shell crimp 13 is crimped over the outward flare 20 of the upper shield 10 to complete the sealing process. The lower shield 14 is installed and crimped into place on the lower surface of the protruding end of the sensor element 6 to complete assembly. During assembly, when force is initially applied to the upper support disk 3, the upper support disk 3 evenly distributes the compression force to the talc disk 2. When the force is increased during assembly, however, the upper support disk 3 will deform from its original planar form into a convex form. In this form, the outside edge of the upper support disk 3 will be disposed closer to the lower support disk 4 than will the center of the upper support disk 3, and the aperture in the upper support disk 3 will be disposed closer to the mat support 8 than will the edge of the upper support disk 3. The net effect of the deformation is to increase the length of the portion of the sensor element 6 that is bound by the talc disk 2. That is, as convexity increases, the talc disk 2 thickens in the center and thins on the edge. Additionally, as the upper support disk 3 is deformed into a convex shape, the compression forces acting on the talc disk 2 are directed inward toward the sensor element 6, which causes better sealing of the sensor element 6 with talc.

After installation into an exhaust system, exhaust gases contact the sensor element 6 on its lower extremity within the lower shield 14, which is perforated to allow for exhaust gas flow. Exhaust gases that reach the lower support disk 4 are prevented from penetrating any further into the sensor by the newly formed talc seal. The entire assembly is held together by compression forces, and is secured by crimping, and the talc seal is thus protected from mechanical breakdown.

One skilled in the art will recognize that the present invention solves the problem of exhaust gas infiltration into the body of a mat-supported exhaust sensor; whereas conventional mat-supported exhaust sensors allow some passage of fumes into the body of the exhaust sensor shell, the present invention seals the exhaust sensor 100 interior from the exhaust gas flow, preventing exhaust gases from infiltrating a clean air reference chamber within the exhaust sensor 100. Since the support disks 3,4 used in the present invention can be made of relatively thin metal instead of ceramic (i.e., a more ductile material), the sensor size can be significantly reduced without any loss of functionality. For example, typical ceramic disks are about 5 mm thick or greater, while the metallic support disks of the present invention can be about 1.5 mm thick or less.

Additionally, although the metal support disks 3,4 can be up to three times more thermally conductive than the prior art ceramic disks, there is reduced thermal conductivity. Essentially, since the operational thickness of the metal of the present invention is so much less than that for ceramic, the added thermal conductivity of the metal is negated, and overall thermal conductivity drops. The thinner metal support disks 3,4 allow for a smaller overall unit, and commensurately less expensive construction.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An exhaust sensor, comprising:
   a shell;
   a talc assembly concentrically disposed within said shell, said talc assembly having a deformable talc disk disposed between a first support disk and a second support disk, wherein at least one of said support disks is metal;
   a planar sensor element disposed through said shell and said talc assembly; and
   a mat support disposed around at least a portion of said sensor element and adjacent to said first support disk;
   wherein said talc disk forms a seal against said shell and said sensor element.

2. The exhaust sensor of claim 1, further comprising;
   a crimp disposed on said shell;
   an inner shield disposed around said mat support and between said mat support and said shell;
   an upper shield disposed around at least a portion of said inner shield and having a flared end, wherein said flared end is adjacent to and in intimate contact with said crimp.

3. The exhaust sensor of claim 2, further comprising:
   a push ring having a bend, wherein said push ring is disposed between said inner shield and said shell, said push ring is adjacent to and physically contacts said first support disk, and said bend is disposed adjacent to said flared end.

4. The exhaust sensor of claim 1, wherein said metal is a ferrous material, or is an alloy thereof.

5. An exhaust sensor, comprising:
   a shell;
   a talc assembly concentrically disposed within said shell, said talc assembly having a deformable talc disk disposed between a first support disk and a second support disk, wherein at least said first support disk is metal and wherein said first support disk is deformed into a convex shape when force is applied;
   a planar sensor element disposed through said shell and said talc assembly; wherein said talc disk forms a seal against said shell and said sensor element; and
   a mat support disposed around at least a portion of said sensor element and adjacent to said first support disk.

6. The exhaust sensor of claim 5, comprising an inner shield which is in physical contact with said first support disk.

7. The inner shield of claim 6, wherein the inner shield deforms the said first support disk into a convex shape once force is applied to the said exhaust sensor.

* * * * *